United States Patent
Kubo et al.

(10) Patent No.: US 7,425,454 B2
(45) Date of Patent: Sep. 16, 2008

(54) BIOSENSOR

(75) Inventors: Toshiaki Kubo, Kanagawa (JP); Masaki Noro, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 241 days.

(21) Appl. No.: 11/190,864

(22) Filed: Jul. 28, 2005

(65) Prior Publication Data

US 2006/0128032 A1 Jun. 15, 2006

(30) Foreign Application Priority Data

Aug. 2, 2004 (JP) ............................. 2004-225130

(51) Int. Cl.
*G01N 33/543* (2006.01)

(52) U.S. Cl. ..................... 436/518; 436/164; 436/524; 436/525; 436/527; 436/805

(58) Field of Classification Search ...................... None
See application file for complete search history.

(56) References Cited

U.S. PATENT DOCUMENTS

| 4,804,709 | A | * | 2/1989 | Takago et al. ............... 525/102 |
| 5,236,667 | A | * | 8/1993 | Puschett et al. .......... 422/82.11 |
| 5,242,828 | A | | 9/1993 | Bergstrom |
| 5,627,079 | A | * | 5/1997 | Gardella, Jr. et al. ........ 436/525 |
| 6,432,723 | B1 | * | 8/2002 | Plaxco et al. ............... 436/518 |
| 6,444,254 | B1 | | 9/2002 | Chilkoti et al. |
| 2005/0008851 | A1 | | 1/2005 | Ezoe et al. |

* cited by examiner

*Primary Examiner*—Christopher L Chin
(74) *Attorney, Agent, or Firm*—Sughrue Mion, PLLC

(57) ABSTRACT

It is an object of the present invention to provide a detection surface used for biosensors, in which non-specific adsorption is suppressed and the generation of pinholes is also suppressed. The present invention provides a biosensor, which comprises a substrate coated with a hydrophobic polymer having an alkyl group substituted with a fluorine atom.

2 Claims, No Drawings

BIOSENSOR

TECHNICAL FIELD

The present invention relates to a biosensor and a method for analyzing an interaction between biomolecules using the biosensor. Particularly, the present invention relates to a biosensor which is used for a surface plasmon resonance biosensor and a method for analyzing an interaction between biomolecules using the biosensor.

BACKGROUND ART

Recently, a large number of measurements using intermolecular interactions such as immune responses are being carried out in clinical tests, etc. However, since conventional methods require complicated operations or labeling substances, several techniques are used that are capable of detecting the change in the binding amount of a test substance with high sensitivity without using such labeling substances. Examples of such a technique may include a surface plasmon resonance (SPR) measurement technique, a quartz crystal microbalance (QCM) measurement technique, and a measurement technique of using functional surfaces ranging from gold colloid particles to ultra-fine particles. The SPR measurement technique is a method of measuring changes in the refractive index near an organic functional film attached to the metal film of a chip by measuring a peak shift in the wavelength of reflected light, or changes in amounts of reflected light in a certain wavelength, so as to detect adsorption and desorption occurring near the surface. The OCM measurement technique is a technique of detecting adsorbed or desorbed mass at the ng level, using a change in frequency of a crystal due to adsorption or desorption of a substance on gold electrodes of a quartz crystal (device). In addition, the ultra-fine particle surface (nm level) of gold is functionalized, and physiologically active substances are immobilized thereon. Thus, a reaction to recognize specificity among physiologically active substances is carried out, thereby detecting a substance associated with a living organism from sedimentation of gold fine particles or sequences.

In all of the above-described techniques, the surface where a physiologically active substance is immobilized is important. Surface plasmon resonance (SPR), which is most commonly used in this technical field, will be described below as an example.

A commonly used measurement chip comprises a transparent substrate (e.g., glass), an evaporated metal film, and a thin film having thereon a functional group capable of immobilizing a physiologically active substance. The measurement chip immobilizes the physiologically active substance on the metal surface via the functional group. A specific binding reaction between the physiological active substance and a test substance is measured, so as to analyze an interaction between biomolecules.

As a thin film having a functional group capable of immobilizing a physiologically active substance, there has been reported a measurement chip where a physiologically active substance is immobilized by using a functional group binding to metal, a linker with a chain length of 10 or more atoms, and a compound having a functional group capable of binding to the physiologically active substance (Japanese Patent No. 2815120). Moreover, a measurement chip comprising a metal film and a plasma-polymerized film formed on the metal film has been reported (Japanese Patent Laid-Open No. 9-264843).

On the other hand, when a specific binding reaction is measured between a physiologically active substance and a test substance, the test substance does not necessarily consist of a single component, but it is sometimes required to measure the test substance existing in a heterogeneous system, such as in a cell extract. In such a case, if various contaminants such as proteins or lipids were non-specifically adsorbed on the detection surface, detection sensitivity in measurement would significantly be decreased. The aforementioned detection surface has been problematic in that such non-specific adsorption often takes place thereon.

In order to solve such a problem, several methods have been studied. For example, a method of immobilizing hydrophilic hydrogel on a metal surface via a linker, so as to suppress physical adsorption, has been applied (Japanese Patent No. 2815120, U.S. Pat. No. 5,436,161, and Japanese Patent Laid-Open No. 8-193948). However, the ability to suppress non-specific adsorption of this method has not yet been sufficient.

DISCLOSURE OF INVENTION

As a biosensor for suppressing the aforementioned non-specific adsorption, a biosensor comprising a substrate coated with a hydrophobic polymer has been proposed (Japanese Patent Laid-Open No. 2004-271514). Such a biosensor comprising a substrate coated with a hydrophobic polymer can suppress non-specific adsorption. However, this biosensor has been problematic in that pinholes are generated as a result of a hydrolysis treatment depending on the type of a hydrophobic polymer, and that a metal surface is exposed in some cases. Even if such pinholes are generated, when a substance with a relatively large molecular weight, such as a protein, is analyzed, there are no significant influences. However, in the case of analyzing a compound with a small molecular weight, which strongly interacts with gold, it may cause some trouble. It is an object of the present invention to solve the aforementioned problems. In other words, it is an object of the present invention to provide a detection surface used for biosensors, in which non-specific adsorption is suppressed and the generation of pinholes is also suppressed.

As a result of intensive studies directed towards achieving the aforementioned object, the present inventors have found that a biosensor, in which non-specific adsorption and the generation of pinholes are suppressed, can be provided by coating the surface of a substrate with a hydrophobic polymer having an alkyl group substituted with a fluorine atom, thereby completing the present invention.

Thus, the present invention provides a biosensor, which comprises a substrate coated with a hydrophobic polymer having an alkyl group substituted with a fluorine atom.

Preferably, the biosensor of the present invention comprises a metal surface or metal film coated with a hydrophobic polymer having an alkyl group substituted with a fluorine atom.

Preferably, the metal surface or metal film consists of a free electron metal selected from the group consisting of gold, silver, copper, platinum, and aluminum.

Preferably, wherein the coating thickness of the hydrophobic polymer having an alkyl group substituted with a fluorine atom is between 0.1 nm and 500 nm, and more preferably between 0.5 nm and 200 nm.

Preferably, the biosensor of the present invention has a functional group capable of immobilizing a physiologically active substance on the outermost surface of the substrate.

Preferably, the functional group capable of immobilizing a physiologically active substance is —OH, —SH, —COOH, —$NR^1R^2$ (wherein each of $R^1$ and $R^2$ independently represents a hydrogen atom or lower alkyl group), —CHO, —$NR^3NR^1R^2$ (wherein each of $R^1$, $R^2$ and $R^3$ independently represents a hydrogen atom or lower alkyl group), —NCO, —NCS, an epoxy group, or a vinyl group.

Preferably, the biosensor of the present invention can be produced by contacting the substrate with a solution of a hydrophobic polymer having an alkyl group substituted with a fluorine atom, and then contacting the substrate with a liquid which does not contain said polymer.

Preferably, the biosensor of the present invention is used in non-electrochemical detection, and more preferably in surface plasmon resonance analysis.

Another aspect of the present invention provides a method for producing the biosensor according to the present invention, which comprises steps of coating a substrate with a hydrophobic polymer having an alkyl group substituted with a fluorine atom.

Preferably, the substrate may be contacted with a solution of a hydrophobic polymer having an alkyl group substituted with a fluorine atom, and then the substrate may be contacted with a liquid which does not contain said polymer.

Another aspect of the present invention provides the biosensor according to the present invention, wherein a physiologically active substance is bound to the surface by covalent bonding.

Another aspect of the present invention provides a method for immobilizing a physiologically active substance on a biosensor, which comprises a step of allowing a physiologically active substance to come into contact with the biosensor according to the present invention, so as to allow said physiologically active substance to bind to the surface of said biosensor via a covalent bond.

Another aspect of the present invention provides a method for detecting or measuring a substance interacting with a physiologically active substance, which comprises a step of allowing a test substance to come into contact with the biosensor according to the present invention to the surface of which the physiologically active substance binds via a covalent bond.

Preferably, the substance interacting with the physiologically active substance is detected or measured by a non-electrochemical method. More preferably, the substance interacting with the physiologically active substance is detected or measured by surface plasmon resonance analysis.

BEST MODE FOR CARRYING OUT THE INVENTION

The embodiments of the present invention will be described below.

The biosensor of the present invention is characterized in that it comprises a substrate coated with a hydrophobic polymer having an alkyl group substituted with a fluorine atom.

The biosensor of the present invention has as broad a meaning as possible, and the term biosensor is used herein to mean a sensor, which converts an interaction between biomolecules into a signal such as an electric signal, so as to measure or detect a target substance. The conventional biosensor is comprised of a receptor site for recognizing a chemical substance as a detection target and a transducer site for converting a physical change or chemical change generated at the site into an electric signal. In a living body, there exist substances having an affinity with each other, such as enzyme/substrate, enzyme/coenzyme, antigen/antibody, or hormone/receptor. The biosensor operates on the principle that a substance having an affinity with another substance, as described above, is immobilized on a substrate to be used as a molecule-recognizing substance, so that the corresponding substance can be selectively measured.

A hydrophobic polymer having an alkyl group substituted with a fluorine atom used in the present invention is a polymer having no water-absorbing properties. Its solubility in water (25° C.) is 10% or less, more preferably 1% or less, and most preferably 0.1% or less.

A hydrophobic monomer which forms a hydrophobic polymer having an alkyl group substituted with a fluorine atom can be selected from vinyl esters, acrylic esters, methacrylic esters, olefins, styrenes, crotonic esters, itaconic diesters, maleic diesters, fumaric diesters, allyl compounds, vinyl ethers, vinyl ketones, or the like. The hydrophobic polymer may be either a homopolymer consisting of one type of monomer, or copolymer consisting of two or more types of monomers.

Such a hydrophobic polymer having an alkyl group substituted with a fluorine atom used in the present invention preferably has a fluorinated alkyl group as an ester in a molecule thereof. In particular, acrylic ester and methacrylic ester are preferable.

Such a fluorinated alkyl group may be a linear, branched, or cyclic group containing 1 or more carbon atoms. (Hereinafter, an alkyl group substituted with a fluorine atom is referred to as "Rf.")

Rf is an alkyl group containing 1 or more carbon atoms, which is substituted with at least one fluorine atom. Rf may be substituted with at least one fluorine atom, and may have a linear, branched, or cyclic structure. In addition, such Rf may further be substituted with substituents other than a fluorine atom, or it may be substituted only with a fluorine atom.

Examples of substituents other than a fluorine atom for Rf may include an alkenyl group, an aryl group, an alkoxyl group, halogen atoms other than a fluorine atom, a carboxylic ester group, a carbonamide group, a carbamoyl group, an oxycarbonyl group, and a phosphoric ester group.

As Rf, a fluorine-substituted alkyl group containing 1 to 16 carbon atoms is preferable, a fluorine-substituted alkyl group containing 1 to 12 carbon atoms is more preferable, and a fluorine-substituted alkyl group containing 4 to 10 carbon atoms is further more preferable. Preferred examples of such Rf are given below.

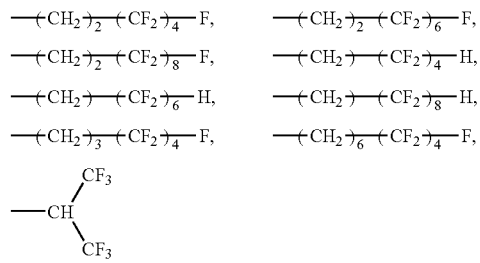

Rf is further preferably an alkyl group containing 4 to 10 carbon atoms, the terminus of which is substituted with a trifluoromethyl group, and is particularly preferably an alkyl group containing 3 to 10 carbon atoms which is represented by —$(CH_2)_{n1}$—$(CF_2)_{n2}F$ wherein $n^1$ represents an integer between 1 and 6, and $n^2$ represents an integer between 3 and 8. Specific examples of Rf may include —$CH_2$—$(CF_2)_2F$, —$(CH_2)_6$—$(CF_2)_4F$, —$(CH_2)_3$—$(CF_2)_4F$, —$CH_2$—$(CF_2)_3F$, —$(CH_2)_2$—$(CF_2)_4F$, —$(CH_2)_3$—$(CF_2)_4F$, —$(CH_2)_6$—$(CF_2)_4F$, —$(CH_2)_2$—$(CF_2)_6F$, —$(CH_2)_3$—$(CF_2)_6F$, and —$(CH_2)_2$—$(CF_2)_6F$. Of these, —$(CH_2)_2$—$(CF_2)_4F$ and —$(CH_2)_2$—$(CF_2)_6F$ are most preferable.

A hydrophobic polymer having an alkyl group substituted with a fluorine atom used in the present invention may also be a copolymer with other monomers. In such a case, preferred examples of a copolymer may include methacrylic esters such as methyl methacrylate, acrylic esters such as methyl acrylate, and styrene.

Specific examples of a hydrophobic polymer having an alkyl group substituted with a fluorine atom are given below.

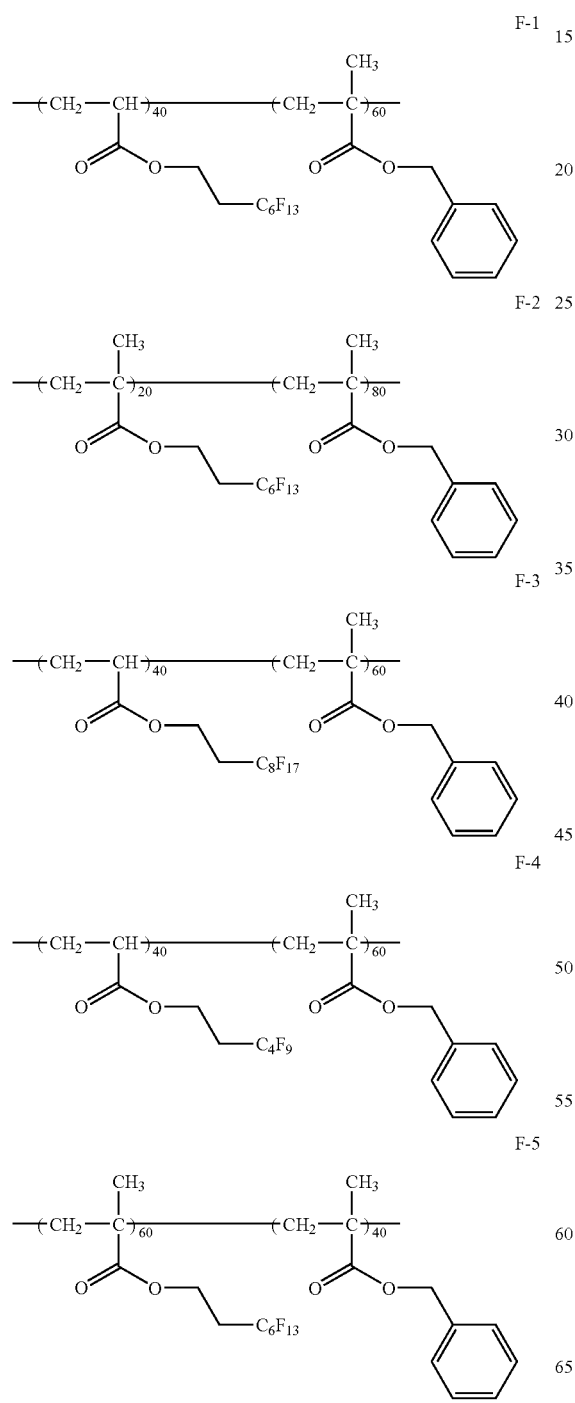

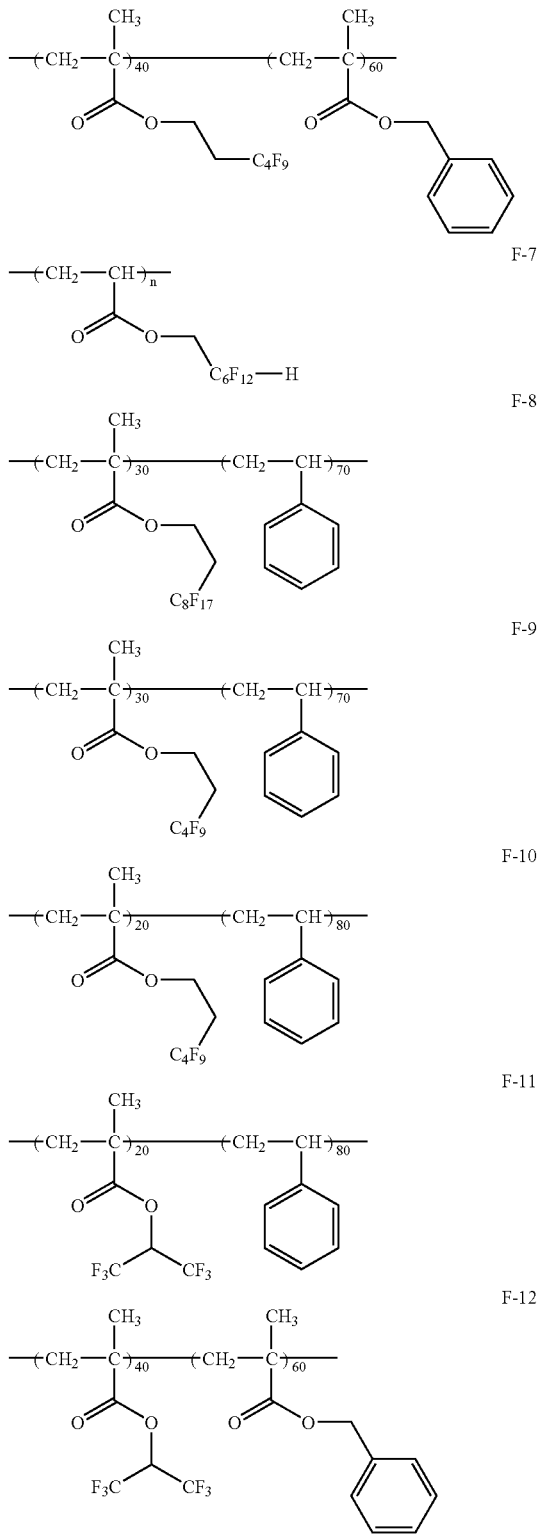

A substrate can be coated with a hydrophobic polymer having an alkyl group substituted with a fluorine atom (hereinafter also referred to as "hydrophobic polymer") according to common methods. Examples of such a coating method may include spin coating, air knife coating, bar coating, blade coating, slide coating, curtain coating, spray method, evaporation method, cast method, and dip method.

In the dip method, coating is carried out by contacting a substrate with a solution of the hydrophobic polymer, and then with a liquid which does not contain the hydrophobic polymer. Preferably, the solvent of the solution of a hydrophobic polymer is the same as that of the liquid which does not contain said hydrophobic polymer.

In the dip method, a layer of a hydrophobic polymer having an uniform coating thickness can be obtained on a surface of a substrate regardless of inequalities, curvature and shape of the substrate by suitably selecting a coating solvent for hydrophobic polymer.

The type of coating solvent used in the dip method is not particularly limited, and any solvent can be used so long as it can dissolve a part of a hydrophobic polymer. Examples thereof include formamide solvents such as N,N-dimethylformamide, nitrile solvents such as acetonitrile, alcohol solvents such as phenoxyethanol, ketone solvents such as 2-butanone, and benzene solvents such as toluene, but are not limited thereto.

In the solution of a hydrophobic polymer which is contacted with a substrate, the hydrophobic polymer may be dissolved completely, or alternatively, the solution may be a suspension which contains undissolved component of the hydrophobic polymer. The temperature of the solution is not particularly limited, so long as the state of the solution allows a part of the hydrophobic polymer to be dissolved. The temperature is preferably −20° C. to 100° C. The temperature of the solution may be changed during the period when the substrate is contacted with a solution of a hydrophobic polymer. The concentration of the hydrophobic polymer in the solution is not particularly limited, and is preferably 0.01% to 30%, and more preferably 0.1% to 10%.

The period for contacting the solid substrate with a solution of a hydrophobic polymer is not particularly limited, and is preferably 1 second to 24 hours, and more preferably 3 seconds to 1 hour.

As the liquid which does not contain the hydrophobic polymer, it is preferred that the difference between the SP value (unit: $(J/cm^3)^{1/2}$) of the solvent itself and the SP value of the hydrophobic polymer is 1 to 20, and more preferably 3 to 15. The SP value is represented by a square root of intermolecular cohesive energy density, and is referred to as solubility parameter. In the present invention, the SP value $\delta$ was calculated by the following formula. As the cohesive energy (Ecoh) of each functional group and the mol volume (V), those defined by Fedors were used (R. F. Fedors, Polym.Eng.Sci., 14(2) P147, P472(1974)).

$$\delta = (\Sigma Ecoh/\Sigma V)^{1/2}$$

Examples of the SP values of the hydrophobic polymers and the solvents are shown below;

Solvent: 2-phenoxyethanol: 25.3 against polymethylmethacrylate-polystyrene copolymer (1:1): 21.0
Solvent: acetonitrile: 22.9 against polymethylmethacrylate: 20.3
Solvent: toluene: 18.7 against polystyrene: 21.6

The period for contacting a substrate with a liquid which does not contain the hydrophobic polymer is not particularly limited, and is preferably 1 second to 24 hours, and more preferably 3 seconds to 1 hour. The temperature of the liquid is not particularly limited, so long as the solvent is in a liquid state, and is preferably −20° C. to 100° C. The temperature of the liquid may be changed during the period when the substrate is contacted with the solvent. When a less volatile solvent is used, the less volatile solvent may be substituted with a volatile solvent which can be dissolved in each other after the substrate is contacted with the less volatile solvent, for the purpose of removing the less volatile solvent.

The coating thickness of a hydrophobic polymer is not particularly limited, but it is preferably between 0.1 nm and 500 nm, and particularly preferably between 1 nm and 300 nm.

Preferably, the metal surface or metal film of the biosensor of the present invention is coated with a hydrophobic polymer having an alkyl group substituted with a fluorine atom. A metal constituting the metal surface or metal film is not particularly limited, as long as surface plasmon resonance is generated when the metal is used for a surface plasmon resonance biosensor. Examples of a preferred metal may include free-electron metals such as gold, silver, copper, aluminum or platinum. Of these, gold is particularly preferable. These metals can be used singly or in combination. Moreover, considering adherability to the above substrate, an interstitial layer consisting of chrome or the like may be provided between the substrate and a metal layer.

The film thickness of a metal film is not limited. When the metal film is used for a surface plasmon resonance biosensor, the thickness is preferably between 0.1 nm and 500 nm, and particularly preferably between 1 nm and 200 nm. If the thickness exceeds 500 nm, the surface plasmon phenomenon of a medium cannot be sufficiently detected. Moreover, when an interstitial layer consisting of chrome or the like is provided, the thickness of the interstitial layer is preferably between 0.1 nm and 10 nm.

Formation of a metal film may be carried out by common methods, and examples of such a method may include sputtering method, evaporation method, ion plating method, electroplating method, and nonelectrolytic plating method.

A metal film is preferably placed on a substrate. The description "placed on a substrate" is used herein to mean a case where a metal film is placed on a substrate such that it directly comes into contact with the substrate, as well as a case where a metal film is placed via another layer without directly coming into contact with the substrate. When a substrate used in the present invention is used for a surface plasmon resonance biosensor, examples of such a substrate may include, generally, optical glasses such as BK7, and synthetic resins. More specifically, materials transparent to laser beams, such as polymethyl methacrylate, polyethylene terephthalate, polycarbonate or a cycloolefin polymer, can be used. For such a substrate, materials that are not anisotropic with regard to polarized light and have excellent workability are preferably used.

The biosensor of the present invention comprising a substrate coated with a hydrophobic polymer having an alkyl group substituted with a fluorine atom preferably has a functional group capable of immobilizing a physiologically active substance on the outermost surface of the substrate. The term "the outermost surface of the substrate" is used to mean "the surface, which is farthest from the substrate," and more specifically, it means "the surface of a hydrophobic polymer applied on a substrate, which is farthest from the substrate."

Examples of a preferred functional group may include —OH, —SH, —COOH, —NR$^1$R$^2$ (wherein each of R$^1$ and R$^2$ independently represents a hydrogen atom or lower alkyl group), —CHO, —NR$^3$NR$^1$R$^2$ (wherein each of R$^1$, R$^2$ and R$^3$ independently represents a hydrogen atom or lower alkyl group), —NCO, —NCS, an epoxy group, and a vinyl group. The number of carbon atoms contained in the lower alkyl group is not particularly limited herein. However, it is generally about C1 to C10, and preferably C1 to C6.

In order to introduce these functional groups into the outermost surface, a method is applied that involves applying a hydrophobic polymer containing a precursor of such a functional group on a metal surface or metal film, and then generating the functional group from the precursor located on the outermost surface by chemical treatment. For example, polymethyl methacrylate, a hydrophobic polymer containing —COOCH$_3$ group is coated on a metal film, and then the surface comes into contact with an NaOH aqueous solution (1N) at 40° C. for 16 hours, so that a —COOH group is generated on the outermost surface.

A physiologically active substance is covalently bound to the above-obtained surface for a biosensor via the above functional group, so that the physiologically active substance can be immobilized on the metal surface or metal film.

A physiologically active substance immobilized on the surface for the biosensor of the present invention is not particularly limited, as long as it interacts with a measurement target. Examples of such a substance may include an immune protein, an enzyme, a microorganism, nucleic acid, a low molecular weight organic compound, a nonimmune protein, an immunoglobulin-binding protein, a sugar-binding protein, a sugar chain recognizing sugar, fatty acid or fatty acid ester, and polypeptide or oligopeptide having a ligand-binding ability.

Examples of an immune protein may include an antibody whose antigen is a measurement target, and a hapten. Examples of such an antibody may include various immunoglobulins such as IgG, IgM, IgA, IgE or IgD. More specifically, when a measurement target is human serum albumin, an anti-human serum albumin antibody can be used as an antibody. When an antigen is an agricultural chemical, pesticide, methicillin-resistant *Staphylococcus aureus*, antibiotic, narcotic drug, cocaine, heroin, crack or the like, there can be used, for example, an anti-atrazine antibody, anti-kanamycin antibody, anti-metamphetamine antibody, or antibodies against O antigens 26, 86, 55, 111 and 157 among enteropathogenic *Escherichia coli*.

An enzyme used as a physiologically active substance herein is not particularly limited, as long as it exhibits an activity to a measurement target or substance metabolized from the measurement target. Various enzymes such as oxidoreductase, hydrolase, isomerase, lyase or synthetase can be used. More specifically, when a measurement target is glucose, glucose oxidase is used, and when a measurement target is cholesterol, cholesterol oxidase is used. Moreover, when a measurement target is an agricultural chemical, pesticide, methicillin-resistant *Staphylococcus aureus*, antibiotic, narcotic drug, cocaine, heroin, crack or the like, enzymes such as acetylcholine esterase, catecholamine esterase, noradrenalin esterase or dopamine esterase, which show a specific reaction with a substance metabolized from the above measurement target, can be used.

A microorganism used as a physiologically active substance herein is not particularly limited, and various microorganisms such as *Escherichia coli* can be used.

As nucleic acid, those complementarily hybridizing with nucleic acid as a measurement target can be used. Either DNA (including cDNA) or RNA can be used as nucleic acid. The type of DNA is not particularly limited, and any of native DNA, recombinant DNA produced by gene recombination and chemically synthesized DNA may be used.

As a low molecular weight organic compound, any given compound that can be synthesized by a common method of synthesizing an organic compound can be used.

A nonimmune protein used herein is not particularly limited, and examples of such a nonimmune protein may include avidin (streptoavidin), biotin, and a receptor.

Examples of an immunoglobulin-binding protein used herein may include protein A, protein G, and a rheumatoid factor (RF).

As a sugar-binding protein, for example, lectin is used.

Examples of fatty acid or fatty acid ester may include stearic acid, arachidic acid, behenic acid, ethyl stearate, ethyl arachidate, and ethyl behenate.

When a physiologically active substance is a protein such as an antibody or enzyme or nucleic acid, an amino group, thiol group or the like of the physiologically active substance is covalently bound to a functional group located on a metal surface, so that the physiologically active substance can be immobilized on the metal surface.

A biosensor to which a physiologically active substance is immobilized as described above can be used to detect and/or measure a substance which interacts with the physiologically active substance.

Thus, the present invention provides a method of detecting and/or measuring a substance interacting with the physiologically active substance immobilized to the biosensor of the present invention, to which a physiologically active substance is immobilized, wherein the biosensor is contacted with a test substance.

As such a test substance, for example, a sample containing the above substance interacting with the physiologically active substance can be used.

In the present invention, it is preferable to detect and/or measure an interaction between a physiologically active substance immobilized on the surface used for a biosensor and a test substance by a nonelectric chemical method. Examples of a non-electrochemical method may include a surface plasmon resonance (SPR) measurement technique, a quartz crystal microbalance (QCM) measurement technique, and a measurement technique that uses functional surfaces ranging from gold colloid particles to ultra-fine particles.

In a preferred embodiment of the present invention, the biosensor of the present invention can be used as a biosensor for surface plasmon resonance which is characterized in that it comprises a metal film placed on a transparent substrate.

A biosensor for surface plasmon resonance is a biosensor used for a surface plasmon resonance biosensor, meaning a member comprising a portion for transmitting and reflecting light emitted from the sensor and a portion for immobilizing a physiologically active substance. It may be fixed to the main body of the sensor or may be detachable.

The surface plasmon resonance phenomenon occurs due to the fact that the intensity of monochromatic light reflected from the border between an optically transparent substance such as glass and a metal thin film layer depends on the refractive index of a sample located on the outgoing side of the metal. Accordingly, the sample can be analyzed by measuring the intensity of reflected monochromatic light.

A device using a system known as the Kretschmann configuration is an example of a surface plasmon measurement device for analyzing the properties of a substance to be measured using a phenomenon whereby a surface plasmon is excited with a lightwave (for example, Japanese Patent Laid-Open No. 6-167443). The surface plasmon measurement device using the above system basically comprises a dielectric block formed in a prism state, a metal film that is formed on a face of the dielectric block and comes into contact with a measured substance such as a sample solution, a light source for generating a light beam, an optical system for allowing the above light beam to enter the dielectric block at various angles so that total reflection conditions can be obtained at the interface between the dielectric block and the metal film, and a light-detecting means for detecting the state of surface plasmon resonance, that is, the state of attenuated total reflection, by measuring the intensity of the light beam totally reflected at the above interface.

In order to achieve various incident angles as described above, a relatively thin light beam may be caused to enter the above interface while changing an incident angle. Otherwise, a relatively thick light beam may be caused to enter the above interface in a state of convergent light or divergent light, so that the light beam contains components that have entered therein at various angles. In the former case, the light beam whose reflection angle changes depending on the change of the incident angle of the entered light beam can be detected with a small photodetector moving in synchronization with the change of the above reflection angle, or it can also be detected with an area sensor extending along the direction in which the reflection angle is changed. In the latter case, the light beam can be detected with an area sensor extending to a direction capable of receiving all the light beams reflected at various reflection angles.

With regard to a surface plasmon measurement device with the above structure, if a light beam is allowed to enter the metal film at a specific incident angle greater than or equal to a total reflection angle, then an evanescent wave having an electric distribution appears in a measured substance that is in contact with the metal film, and a surface plasmon is excited by this evanescent wave at the interface between the metal film and the measured substance. When the wave vector of the evanescent light is the same as that of a surface plasmon and thus their wave numbers match, they are in a resonance state, and light energy transfers to the surface plasmon. Accordingly, the intensity of totally reflected light is sharply decreased at the interface between the dielectric block and the metal film. This decrease in light intensity is generally detected as a dark line by the above light-detecting means. The above resonance takes place only when the incident beam is p-polarized light. Accordingly, it is necessary to set the light beam in advance such that it enters as p-polarized light.

If the wave number of a surface plasmon is determined from an incident angle causing the attenuated total reflection (ATR), that is, an attenuated total reflection angle ($\theta SP$), the dielectric constant of a measured substance can be determined. As described in Japanese Patent Laid-Open No. 11-326194, a light-detecting means in the form of an array is considered to be used for the above type of surface plasmon measurement device in order to measure the attenuated total reflection angle ($\theta SP$) with high precision and in a large dynamic range. This light-detecting means comprises multiple photo acceptance units that are arranged in a certain direction, that is, a direction in which different photo acceptance units receive the components of light beams that are totally reflected at various reflection angles at the above interface.

In the above case, there is established a differentiating means for differentiating a photodetection signal outputted from each photo acceptance unit in the above array-form light-detecting means with regard to the direction in which the photo acceptance unit is arranged. An attenuated total reflection angle ($\theta SP$) is then specified based on the derivative value outputted from the differentiating means, so that properties associated with the refractive index of a measured substance are determined in many cases.

In addition, a leaking mode measurement device described in "Bunko Kenkyu (Spectral Studies)" Vol. 47, No. 1 (1998), pp. 21 to 23 and 26 to 27 has also been known as an example of measurement devices similar to the above-described device using attenuated total reflection (ATR). This leaking mode measurement device basically comprises a dielectric block formed in a prism state, a clad layer that is formed on a face of the dielectric block, a light wave guide layer that is formed on the clad layer and comes into contact with a sample solution, a light source for generating a light beam, an optical system for allowing the above light beam to enter the dielectric block at various angles so that total reflection conditions can be obtained at the interface between the dielectric block and the clad layer, and a light-detecting means for detecting the excitation state of waveguide mode, that is, the state of attenuated total reflection, by measuring the intensity of the light beam totally reflected at the above interface.

In the leaking mode measurement device with the above structure, if a light beam is caused to enter the clad layer via the dielectric block at an incident angle greater than or equal to a total reflection angle, only light having a specific wave number that has entered at a specific incident angle is transmitted in a waveguide mode into the light wave guide layer, after the light beam has penetrated the clad layer. Thus, when the waveguide mode is excited, almost all forms of incident light are taken into the light wave guide layer, and thereby the state of attenuated total reflection occurs, in which the intensity of the totally reflected light is sharply decreased at the above interface. Since the wave number of a waveguide light depends on the refractive index of a measured substance placed on the light wave guide layer, the refractive index of the measurement substance or the properties of the measured substance associated therewith can be analyzed by determining the above specific incident angle causing the attenuated total reflection.

In this leaking mode measurement device also, the above-described array-form light-detecting means can be used to detect the position of a dark line generated in a reflected light due to attenuated total reflection. In addition, the above-described differentiating means can also be applied in combination with the above means.

The above-described surface plasmon measurement device or leaking mode measurement device may be used in random screening to discover a specific substance binding to a desired sensing substance in the field of research for development of new drugs or the like. In this case, a sensing substance is immobilized as the above-described measured substance on the above thin film layer (which is a metal film in the case of a surface plasmon measurement device, and is a clad layer and a light guide wave layer in the case of a leaking mode measurement device), and a sample solution obtained by dissolving various types of test substance in a solvent is added to the sensing substance. Thereafter, the above-described attenuated total reflection angle ($\theta SP$) is measured periodically when a certain period of time has elapsed.

If the test substance contained in the sample solution is bound to the sensing substance, the refractive index of the sensing substance is changed by this binding over time. Accordingly, the above attenuated total reflection angle ($\theta SP$) is measured periodically after the elapse of a certain time, and it is determined whether or not a change has occurred in the above attenuated total reflection angle ($\theta SP$), so that a binding state between the test substance and the sensing substance is measured. Based on the results, it can be determined whether or not the test substance is a specific substance binding to the sensing substance. Examples of such a combination between a specific substance and a sensing substance may include an antigen and an antibody, and an antibody and an antibody. More specifically, a rabbit anti-human IgG antibody is immobilized as a sensing substance on the surface of a thin film layer, and a human IgG antibody is used as a specific substance.

It is to be noted that in order to measure a binding state between a test substance and a sensing substance, it is not always necessary to detect the angle itself of an attenuated total reflection angle ($\theta SP$). For example, a sample solution may be added to a sensing substance, and the amount of an attenuated total reflection angle ($\theta SP$) changed thereby may be measured, so that the binding state can be measured based on the magnitude by which the angle has changed. When the above-described array-form light-detecting means and differentiating means are applied to a measurement device using attenuated total reflection, the amount by which a derivative value has changed reflects the amount by which the attenuated total reflection angle (θSP) has changed. Accordingly, based on the amount by which the derivative value has changed, a binding state between a sensing substance and a test substance can be measured (Japanese Patent Application No. 2000-398309 filed by the present applicant). In a measuring method and a measurement device using such attenuated total reflection, a sample solution consisting of a solvent and a test substance is added dropwise to a cup- or petri dish-shaped measurement chip wherein a sensing substance is immobilized on a thin film layer previously formed at the bottom, and then, the above-described amount by which an attenuated total reflection angle (θSP) has changed is measured.

Moreover, Japanese Patent Laid-Open No. 2001-330560 describes a measurement device using attenuated total reflection, which involves successively measuring multiple measurement chips mounted on a turntable or the like, so as to measure many samples in a short time.

When the biosensor of the present invention is used in surface plasmon resonance analysis, it can be applied as a part of various surface plasmon measurement devices described above.

The present invention will be further specifically described in the following examples. However, the examples are not intended to limit the scope of the present invention.

EXAMPLES

Example 1

Production of Chip used for Biosensors (1) Production of Chip for Biosensors Coated with Polymer (A) Production by Spin-coating A cover glass with a size of 1 cm×1 cm, which had been coated with gold via evaporation resulting in a gold film with a thickness of 50 nm, was treated with a Model-208 UV-ozone cleaning system (TECHNOVISION INC.) for 30 minutes. Thereafter, it was placed in a spin coater (MODEL ASS-303; manufactured by ABLE) and then rotated at 1,000 rpm. 50 µl of a methyl ethyl ketone solution containing each polymer shown in Table 1 (2 mg/ml) was added dropwise to the center of the cover glass coated with gold via evaporation, and 2 minutes later, the rotation was terminated. This sample is called a spin-coated polymer chip.

(B) Production by Immersion Adsorption Method

A cover glass with a size of 1 cm×1 cm, which had been coated with gold via evaporation resulting in a gold film with a thickness of 50 nm, was treated with a Model-208 UV-ozone cleaning system (TECHNOVISION INC.) for 30 minutes. Thereafter, it was immersed in a 1% polymer solution for 30 minutes and then washed with a solvent. This operation was repeated 3 times. Thereafter, the resultant was dried at 25° C. under reduced pressure. This sample is called an immersed polymer chip.

(2) Introduction of COOH Group into Polymer Surface

The polymer chip produced in the above was immersed in an NaOH aqueous solution (1 N) at 40° C. for 1.6 hours, followed by washing with water 3 times. This sample is called a COOH surface chip.

Example 2

Evaluation of Performance of Chip for Biosensors (1) Evaluation of Frequency of Generation of Pinholes The sample produced by the aforementioned methods was immersed in a KI·I2 solution (manufactured by Kanto Chemical Co., Inc.) for 10 seconds. After washing with water, the state of a metal film was observed with an optical microscope. The degree of generation of pinholes on the metal film was evaluated by 5 grades at a magnification of 20 times with a transmitted light. If pinholes exist in the polymer, the KI·I2 solution dissolves gold, and pinholes are thereby generated on the gold film. The results are shown below in Table 1. From the results shown in Table 1, it is found that the generation of pinholes is suppressed by the use of the polymer of the present invention, and that good results are thereby obtained.

(2) Measurement of Non-specific Adsorption

The following experiment was carried out to examine the influence of pinholes on SPR measurement.

The aforementioned samples were placed on the cartridge block of a surface plasmon resonance biosensor (BIACORE 3000; manufactured by Biacore). Thereafter, 50 µl of a solution containing compound A shown below (1 mg/ml, HBS-EP buffer (pH 7.4; manufactured by Biacore)) was fed to a measurement cell at a flow rate of 10 µl/min. The HBS-EP buffer consisted of 0.01 mol/l HEPES (N-2-hydroxyethylpiperazine-N'-2-ethanesulfonic acid) (pH 7.4), 0.15 mol/l NaCl, 0.003 mol/l EDTA, and 0.005% by weight of Surfactant P20. The amount of resonance signal changed (RU value) that was obtained 3 minutes after completion of the pouring of the solution was defined as the amount of non-specific adsorption.

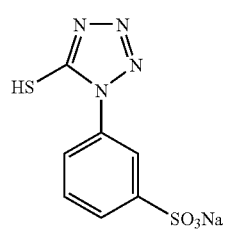

Compound A

In order to eliminate the influence of carboxylic acid, a COOH group was blocked on the surface having such carboxylic acid by the following method using ethanolamine. Each chip was placed on the cartridge block of a commercially available surface plasmon resonance biosensor (BIACORE 3000; manufactured by Biacore). Thereafter, 100 µl of a mixed solution consisting of 1-ethyl-2,3-dimethylaminopropylcarbodiimide (400 mM) and N-hydroxysuccinimide (100 mM) was fed to a measurement cell at a flow rate of 10 µl/min. Thereafter, 100 µl of an ethanolamine-HCl solution (1 M, pH 8.5) was fed to the measurement cell at a flow rate of 10 µl/min.

The results are shown in Table 1. From the results shown in Table 1, it was found that the use of the polymer of the present invention enables suppression of non-specific adsorption.

TABLE 1

| Type of polymer | Application method | Film thickness* | Before generation of carboxylic acid | | After generation of carboxylic acid | | Remarks |
|---|---|---|---|---|---|---|---|
| | | | Pinholes (Sensory evaluation) | Amount of non-specific adsorption (RU) | Pinholes (Sensory evaluation) | Amount of non-specific adsorption (RU) | |
| PMMA (mean molecular weight: 100,000) | Spin-coating | 20 nm | 5 | <5 | 3 | 22 | Comparative example |
| | | 5 nm | 5 | <5 | 2 | 38 | Comparative example |
| | Immersion (DMF) | 5 nm | 5 | <5 | 1 | 89 | Comparative example |
| F-1 (mean molecular weight: 10,000) | Spin-coating | 20 nm | 5 | <5 | 5 | <5 | Present invention |
| | | 5 nm | 5 | <5 | 5 | <5 | Present invention |
| | Immersion (MIBK/IPA = 93/7) | 5 nm | 5 | <5 | 4 | 8 | Present invention |
| F-7 | Spin-coating | 20 nm | 5 | <5 | 5 | <5 | Present invention |
| | | 5 nm | 5 | <5 | 5 | 6 | Present invention |
| | Immersion (MIBK/IPA = 93/7) | 5 nm | 5 | <5 | 4 | 10 | Present invention |

*The film thickness was measured by using the automatic ellipsometer MARY-102 manufactured by Five Lab Co., Ltd.
Generation of pinholes was evaluated by 5 grades, ranging from (5) not generated, to (1) pinholes generated on the entire surface.

EFFECTS OF THE INVENTION

According to the present invention, it became possible to provide a detection surface used for biosensors, in which non-specific adsorption and the generation of pinholes are suppressed.

The invention claimed is:

1. A method for detecting or measuring a substance interacting with a physiologically active substance, which comprises a step of allowing a test substance to come into contact with a biosensor to the surface of which the physiologically active substance binds via a covalent bond, the biosensor comprising a substrate coated with a hydrophobic polymer having an alkyl group substituted with a fluorine atom in a side chain, wherein the substance interacting with the physiologically active substance is detected or measured by a non-electrochemical method.

2. A method for detecting or measuring a substance interacting with a physiologically active substance, which comprises a step of allowing a test substance to come into contact with a biosensor to the surface of which the physiologically active substance binds via a covalent bond, the biosensor comprising a substrate coated with a hydrophobic polymer having an alkyl group substituted with a fluorine atom in a side chain, wherein the substance interacting with the physiologically active substance is detected or measured by surface plasmon resonance analysis.

* * * * *